United States Patent [19]

Spencer et al.

[11] 4,115,461

[45] Sep. 19, 1978

[54] STABILIZED 1,1,1-TRICHLOROETHANE COMPOSITION

[75] Inventors: David R. Spencer; Wesley L. Archer, both of Midland, Mich.

[73] Assignee: The Dow Chemical Company, Midland, Mich.

[21] Appl. No.: 835,474

[22] Filed: Sep. 21, 1977

Related U.S. Application Data

[63] Continuation-in-part of Ser. No. 712,996, Aug. 9, 1976, abandoned.

[51] Int. Cl.$^2$ ............................................. C07C 17/42
[52] U.S. Cl. .............................. 260/652.5 R; 252/171; 252/364
[58] Field of Search .................. 260/652.5 R; 252/364

[56] References Cited

U.S. PATENT DOCUMENTS

| | | | |
|---|---|---|---|
| 3,281,480 | 10/1966 | Hardies | 260/652.5 R |
| 3,878,256 | 4/1975 | Richtzenhain et al. | 260/652.5 R |

Primary Examiner—C. Davis
Attorney, Agent, or Firm—Glwynn R. Baker

[57] ABSTRACT

1,1,1-Trichloroethane is stabilized for use as a replacement for trichloroethylene in vapor degreasing applications by employing from about 3.6 to about 7.6 volume percent based on the total composition of the following components in 1,1,1-trichloroethane:

Volume %
1 to 3 1,4-dioxane
1 to 3 t-amyl alcohol
0.2 to 0.6 nitromethane or a mixture of nitromethane and nitroethane containing up to 75 volume per cent nitroethane
0.5 to 1 1,2-butylene oxide.

2 Claims, 4 Drawing Figures

STABILIZED 1,1,1-TRICHLOROETHANE COMPOSITION

CROSS-REFERENCE TO RELATED APPLICATION

This is a continuation-in-part of our earlier filed application Ser. No. 712,996 filed Aug. 9, 1976, and now abandoned.

BACKGROUND OF INVENTION 1,1,1-Trichloroethane is a widely used industrial cleaning solvent. With the recent restrictions placed on the use of trichloroethylene, as for example, vapor degreasing, more people are substituting 1,1,1-trichloroethane into uses to which the trichloroethylene was employed. Many of these uses place a severe stress on the 1,1,1-trichloroethane. Previous inhibitor systems for the 1,1,1-trichloroethane have been found weak or ineffective in protecting the solvent and/or the parts being cleaned. Thus, it is necessary to find new inhibitor systems for the 1,1,1-trichloroethane which will permit the extended uses industry is making of this useful solvent.

The prior art has added numerous members from most classes of organic compounds in attempts to improve the stability of 1,1,1-trichloroethane to degradation in the presence of heat, metals (particularly aluminum) and water. For example, esters, ethers, amines, cyano compounds, alcohols, ketones, aldehydes and the like have been suggested alone and in combination in the literature and in patents. However, commercial grades of 1,1,1-trichloroethane used in the major industrial countries contain at least one inner ether (an epoxide and/or dioxane, dioxolane, or trioxane), usually a nitroalkane (nitromethane and/or nitroethane) then one or more of the following acetylenic alcohol, nitrile (acetonitrile or β-methoxypropionitrile), ortho ester (trimethyl ortho formate), lower alkanol (t-butyl or t-amyl alcohol), a ketone (methyl ethyl ketone). These compounds account for the components used in the main in the present day inhibitor systems.

One of the largest suppliers used dioxane, nitromethane and butylene oxide for years. However, even this recognized superior system has shown weaknesses in certain fields of use wherein trichloroethylene was previously employed. Such weaknesses are a result of operator's lack of care in maintenance of their equipment, a chore not usually undertaken on a regular basis when trichloroethylene was employed. However, any rusting, heavy metals fines, particularly aluminum, grinding and buffing compounds, lubricant oils and fluxes such as employed in miniature printed circuits increase the degradation of the solvent and create corrosive atmospheres which attack the metal parts being cleaned. In the past, the manufacturers have been able to screen the new uses and monitor the uses. Such is not possible with the widespread usage to which the solvent has been put in recent months.

It is, therefore, an object of the present invention to provide a stabilized grade of 1,1,11-trichloroethane suitable for the severe use conditions encountered in the substitution of 1,1,1-trichloroethane for trichloroethylene

BRIEF DESCRIPTION OF INVENTION

In accordance with the present invention it has been found advantageous to combine 1,4-dioxane, tertiary amyl alcohol, nitromethane and/or nitroethane, and butylene oxide in the hereinafter proportions to stabilize 1,1,1-trichloroethane for industrial usage as a vapor degreasing solvent in applications wherein 1,1,2-trichloroethylene was previously employed.

As aforestated in the Background of Invention, 1,1,1-trichloroethane is a unique chlorinated hydrocarbon solvent having low toxicity and good ecological properties and is gradually replacing trichloroethylene in the vapor degreasing field. In the new use as a vapor degreasing solvent the 1,1,1-trichloroethane comes under severe use conditions, i.e., contact with metal parts containing aluminum, iron, copper, zinc and alloys thereof, acid compositions used in metal finishing operations, oils and resins, i.e., as in printed circuitry manufacture, and the like. Some of these conditions have been met before in the special uses to which 1,1,1-trichloroethane have been put, but the manufacturers and their distributors have taken care to monitor these uses. Today, however, with the widespread and expanding usage attributable largely to the general ban on use of trichloroethylene, monitoring becomes substantially humanly impossible or extremely expensive. Therefore, extensive efforts have been undertaken to prepare a stabilized grade of 1,1,1-trichloroethane which will be suitable for total replacement of trichloroethylene in the industrial area. A further effort was undertaken to employ as inhibitors, compounds in small quantities, compounds which presently appear to have no ecological or safety hazards, and employ only a minor number of compounds and a major proportion of 1,1,1-trichloroethane. Such a formulation has been found in the above set forth invention, to wit:

1 to 3 volume percent 1,4-dioxane;
1 to 3 volume percent t-amyl alcohol;
0.2 to 0.6 volume percent nitromethane, or a mixture of nitromethane and nitroethane containing up to 75 volume percent nitroethane;
0.5 to 1 volume percent butylene oxide.

wherein the total of dioxane and t-amyl alcohol must be 3 volume percent and the total inhibitor concentration must be 3.6 volume percent. It is contemplated the total maximum inhibitor volume will be 7.6 volume percent in order to eliminate any vapor or liquid health hazards which the inhibitors might exhibit in the ambient atmosphere or bodily contact toward humans as well as maintain the potential of creating a flammability problem to the minimum.

It is to be understood that various combinations of the inhibitors named are known to prevent degradation of the 1,1,1-trichloroethane but that they have not been combined in the aforesaid manner or amounts. The results of the enumerated combination establish an unexpected and unique property of the combination in that while the boiling points of the inhibitor components would indicate loss of nitro—methane and butylene oxide, in fact this does not occur. Repeated usage, that is vaporization and condensation in a vapor degreasing operation, drag-out of solvent vapors on parts, with periodic make-up of inhibited solvent to operating volumes have confirmed that each component of the inhibitor systems remains in a sufficient quantity to stabilize the solvent in both the liquid and vapor state over extended continuous periods of time without build-up of high boilers or loss of low boilers.

The preferred composition consists of
2 to 3 percent dioxane;
1 to 2 percent t-amyl alcohol;

0.3 to 0.6 percent nitromethane, or a mixture of nitromethane and nitroethane containing up to 75 volume percent nitroethane;

0.6 to 0.8 percent butylene oxide.

DETAILED DESCRIPTION OF THE INVENTION

Figure 1:
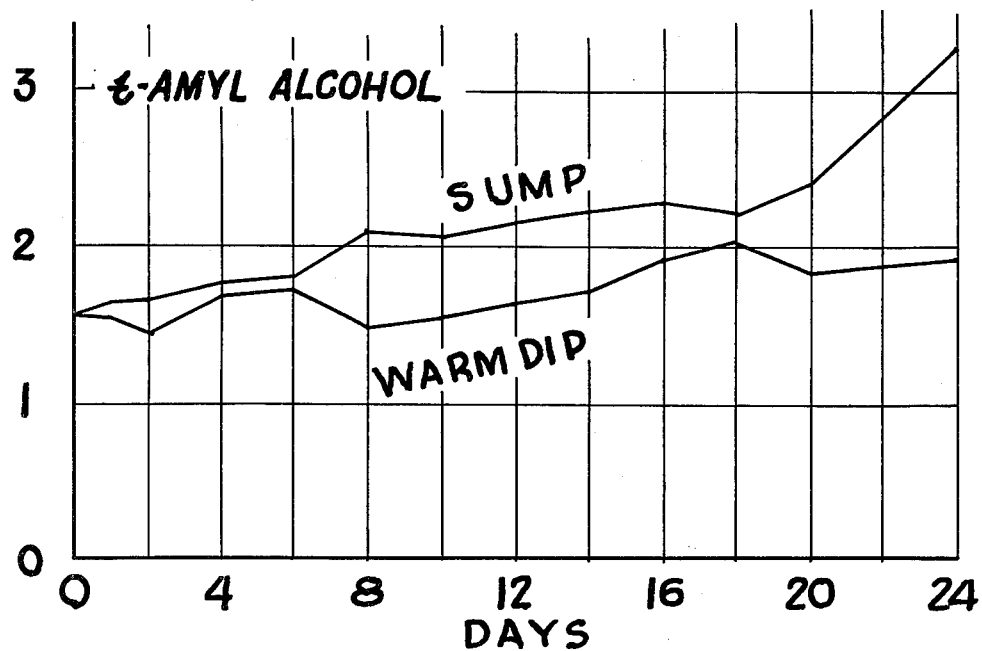

A series of glassware experiments were performed in the laboratory to determine the feasibility of a dioxane/t-amyl alcohol system as the primary aluminum inhibitor. Also, a nitromethane/nitroethane combination was investigated as the secondary metal stabilizer. The following abbreviations will be used throughout: Diox = 1,4-Dioxane, TAA = t-amyl alcohol, BO = 1,2-butylene oxide, NM = nitromethane, NE = nitroethane, bottom = liquid phase, top = vapor condensate phase.

The following 1,1,1-trichloroethane solutions were formulated for testing (all concentrations are as volume percent):

| Formulation Code # | Formulation Composition |
|---|---|
| A | 3.2% Diox, ———, 0.75% BO, 0.4% NM |
| B | 3% Diox, 1% TAA, 0.75% BO, 0.4% NM |
| C | 2% Diox, 2% TAA, 0.75% BO, 0.4% NM |
| D | 2% Diox, 2% TAA, 0.75% BO, 0.2% NM, 0.2% NE |
| E | 2% Diox, 2% TAA, 0.75% BO, ———, 0.4% NE |
| F | 1% Diox, 3% TAA, 0.75% BO, 0.4% NM |
| G | ———, 4% TAA, 0.75% BO, 0.4% NM |

DESCRIPTION AND RESULTS OF EXPERIMENTS

There are three steps in this series of experiments: (1) partitioning; (2) aluminum hot scratch; and, (3) 7-day reflux.

(1) Partitioning (Table I) — each formulation is distilled into two equal fractions (top and bottom) to obtain solutions with inhibitor profiles similar to that found in vapor degreasers. Adequate concentrations of inhibitors in both the boiling liquid phase and the vapor phase of a vapor degreaser is a very important requirement of a good inhibitor package. Therefore the use of inhibitors with proper boiling point ranges and partitioning profiles is important in designing an adequate inhibitor combination. Various combinations of dioxane, t-amyl alcohol, butylene oxide, nitromethane, and nitroethane dissolved in 1,1,1-trichloroethane at various concentrations were distilled into two equal fractions (liquid and vapor phases) to obtain inhibitor profiles from solutions and vapors similar to that found in vapor degreasers. The resulting inhibitor concentrations were obtained by gas chromatographic analysis. Listed below are the average partitioning from the results obtained in the partitioning of the compositions listed in Table I:

|  | % In Vapor Phase | % In Liquid Phase |
|---|---|---|
| Dioxane | 27 | 73 |
| t-Amyl Alcohol | 42 | 58 |
| Nitromethane | 62 | 38 |
| Nitroethane | 34 | 66 |

It can be seen that the distribution of a combination of dioxane and t-amyl alcohol would afford superior protection in both phases than would dioxane alone. Also, it is evident that a 50/50 mix of the two nitroalkanes would give almost equal protection in the two phases.

(2) Aluminum Hot Scratch (Table I) — a series of hot scratch tests were run with 2024 aluminum coupons (Al/Cu alloy) using each original formulation and each top and bottom fraction. This test demonstrates the ability of a stabilizer system to inhibit the 1,1,1-trichloroethane reaction with the aluminum in both the liquid and vapor phases. Specifically, 50 cc of the formulation is placed in a Pyrex petri dish (9 cm diameter by 2.5 cm deep) and placed on a hot plate. The solvent is allowed to heat to just below rolling boil and then taken off the hot plate. A 2024 Al coupon (2½ × ½ × ⅛ inches thick) is immediately placed in the petri dish and the surface of the coupon is scratched with a stylus while the coupon is submerged. Three scratches are made lengthwise of the coupon and five scratches across the coupon. The petri dish is then removed from the hot plate, covered, and observed for one hour. After one hour a "scratch rating" is given to that solution according to the appearance of the scratch sites:

| "Scratch Rating" | Description |
|---|---|
| 0 | Scratches are completely inhibited with no reaction products visible to the eye. |
| 1 | Scratches immediately cure with isolated sites of reaction product. |
| 2 | Scratches rapidly cure but with some formation of reaction products. |
| 3 | Scratches slowly cure with much formation of reaction products. |
| 4 | Little inhibition at scratch sites with a slow continuing reaction. |
| 5 | "Runaway" reaction during the one-hour observation period; the solution turns black, HCl is generated, and a fast ongoing reaction is present at scratch sites. |

TABLE I

| Form. # | Inhibitor | Partitioning Original | Partitioning Top | Partitioning Bottom | Hot Scratch Rating Original | Hot Scratch Rating Top | Hot Scratch Rating Bottom |
|---|---|---|---|---|---|---|---|
| A | % Diox | 3.30 | 1.78 | 4.73 | 0 | 0 | 0 |
|   | % NM | 0.54 | 0.66 | 0.42 | | | |
|   | % BO | 0.71 | 0.83 | 0.59 | | | |
| B | % Diox | 2.96 | 1.65 | 4.20 | 0 | 0 | 0 |
|   | % TAA | 1.06 | 0.90 | 1.20 | | | |
|   | % NM | 0.53 | 0.63 | 0.44 | | | |
|   | % BO | 0.71 | 0.83 | 0.57 | | | |
| C | % Diox | 1.99 | 1.04 | 2.95 | 0 | 1 | 0 |
|   | % TAA | 1.93 | 1.60 | 2.17 | | | |
|   | % NM | 0.50 | 0.63 | 0.38 | | | |
|   | % BO | 0.72 | 0.83 | 0.60 | | | |
| D | % Diox | 1.95 | 1.13 | 2.87 | 0 | 2 | 0 |
|   | % TAA | 2.04 | 1.79 | 2.20 | | | |
|   | % NM | 0.25 | 0.35 | 0.21 | | | |
|   | % NE | 0.21 | 0.17 | 0.29 | | | |
|   | % BO | 0.71 | 0.82 | 0.62 | | | |
| E | % Diox | 2.20 | 1.17 | 2.99 | 0 | 3 | 0 |
|   | % TAA | 2.02 | 1.73 | 2.21 | | | |
|   | % NE | 0.44 | 0.29 | 0.58 | | | |
|   | % BO | 0.71 | 0.80 | 0.60 | | | |
| F | % Diox | 1.06 | 0.56 | 1.52 | 1 | 2 | 0 |
|   | % TAA | 2.73 | 2.31 | 3.16 | | | |
|   | % NM | 0.52 | 0.70 | 0.36 | | | |
|   | % BO | 0.71 | 0.82 | 0.62 | | | |
| G | % TAA | 3.71 | 3.07 | 4.34 | 4 | 5 | 3 |
|   | % NM | 0.42 | 0.60 | 0.50 | | | |
|   | % BO | 0.72 | 0.81 | 0.60 | | | |

It is observed that:

1. As the dioxane concentration decreases and the t-amyl alcohol increases, the ability of the formulation to inhibit the solvent/aluminum reaction decreases.

2. The bottom fraction aluminum hot scratch ratings are better than the ratings for the top fractions due to the higher total primary metal stabilizer present, caused by the partitioning behavior of dioxane and t-amyl alcohol.

3. More protection is afforded due to better partitioning in the vapor phase utilizing dioxane/t-amyl alcohol combinations rather than dioxane alone.

4. Substitution of nitroethane for nitromethane (#C vs. #E) results in less protection in the top fraction due to partitioning of nitroethane favoring the bottom fraction.

5. A 50/50 mix of NM/NE (#D) gives better distribution of nitroalkane in both phases.

6. Tertiary amyl alcohol as the principal inhibitor without dioxane is not an adequate Al stabilizer.

(3) 7-Day Reflux Test — This test consists of refluxing each top and bottom fraction in the presence of metal chips for 7 days. It is a good indication of how effective a stabilizer system would be in preventing 1,1,1-trichloroethane reactions with metals. Each 100 cc fraction was refluxed in the presence of two different sets of metals: (a) 5 grams each 1100 and 2024 aluminum chips and, (b) 5 grams each 70/30 brass chips and iron filings. After 7 days reflux the solutions are filtered and analyzed via gas chromatography for inhibitor losses (Table II).

TABLE II

| Form. # | Initial Inhibitor Concentration | % Lost After 7-Day Reflux | | | |
|---|---|---|---|---|---|
| | | With Al Chips | | With Fe+ Brass Chips | |
| | | Top | Bottom | Top | Bottom |
| A | 3.2% Diox | No Loss (NL) | NL | NL | NL |
| | 0.4% NM | 2 | NL | 1 | 6 |
| | 0.75% BO | NL | 1 | 2 | 7 |
| B | 3% Diox | NL | NL | NL | NL |
| | 1% TAA | NL | NL | NL | NL |
| | 0.4% NM | 5 | 11 | 5 | 13 |
| | 0.75% BO | 2 | 2 | 11 | 14 |
| C | 2% Diox | NL | NL | NL | NL |
| | 2% TAA | NL | NL | 6 | NL |
| | 0.4% NM | 1 | NL | 5 | 5 |
| | 0.75% BO | 2 | 3 | 19 | 12 |
| | 2% Diox | 4 | NL | 7 | NL |
| | 2% TAA | 9 | NL | 6 | NL |
| D | 0.2% NM | 11 | 10 | 17 | 20 |
| | 0.2% NE | 9 | NL | 15 | 4 |
| | 0.75% BO | NL | 4 | 13 | 10 |
| | 2% Diox | 3 | NL | NL | NL |
| | 2% TAA | NL | NL | 6 | NL |
| E | 0.4% NE | NL | 19 | NL | 4 |
| | 0.75% BO | 20 | 58 | 12 | 6 |
| | 1% Diox | NL | NL | NL | NL |
| | 3% TAA | NL | NL | NL | NL |
| F | 0.4% NM | 12 | NL | 13 | NL |
| | 0.75% BO | 2 | 2 | 17 | 17 |
| | 4% TAA | NL | 1 | 3 | 40 |
| G | 0.4% NM | 8 | 44 | 3 | 40 |
| | 0.75% BO | 3 | 41 | 24 | 98 | it is observed that:

1. Inhibitor losses of <20 percent during the 7 days are considered acceptable since the hot scratch tests show protection, i.e., ratings of 0–2, while losses of >20 percent are considered to have failed in preventing metal/1,1,1 reactions since the hot scratch tests show lack of protection. This pass/fail inhibitor loss level is not entirely arbitrary but is based on our wide experience with inhibitor system behavior in industrial vapor degreasing where stabilizer losses of greater than 20–25 percent indicate some solvent decomposition.

2. Comparing #C and #E, it is evident that NE alone is not as effective a secondary inhibitor for Al/1,1,1 reaction as is NM alone. However, an NM/NE mix (#D) is an effective secondary Al stabilizer.

3. TAA alone is not as effective as metal/1,1,1 primary inhibitor as is DIOX alone (#G vs. #A).

4. Combinations of DIOX/TAA do prevent metal/1,1,1 reactions (#B, #C, #D, and #F) and afford better overall inhibitor distribution in top and bottom phases.

DEGREASER TEST

The following formulation was tested in a laboratory sized vapor degreaser: 0.72 percent BO, 1.65 percent TAA, 2.58 percent DIOX, 0.46 percent NM, balance 1,1,1-trichloroethane. This degreaser had a 4-gallon boil sump and a 3-gallon clean dip side (fed from condensed solvent vapors). The degreaser was run at the solvent boiling point uncovered, 24 hours/day, for 24 days. Daily additions of fresh solvent were added to maintain a constant volume. Every effort was made to simulate actual degreasing operations and to subject the solvent formulations to many of the stresses that commonly occur in the field. Various metal alloys (100 g each) were placed in both the boil sump and warm dip. These metals are 2024 aluminum turnings, 70/30 brass turnings, and coarse steel wool; all of which expose a large metal surface area with potential reactive sites to the solvent. A lubricating oil (commonly used in metal machining operations) was added to the boil sump (constituting about 10 percent of the liquid volume of the boil sump). Finally, water was added to the boil sump on the 18th day of the test (constituting about 1 percent of the total degreaser charge).

ANALYTICAL TEST PROCEDURE

Both the boiling sump and the warm dip tank were sampled about every other day. Inhibitor distribution profiles were than obtained by vapor phase chromatography. Also, some of the samples were analyzed via emission spectroscopy for metal ion concentrations (Al Cu, Fe, Zn). This reveals any metal corrosion problems and potential reactions between the solvent and particular metals due to inadequate stabilization.

RESULTS OF DEGREASER TEST

Figure 2:
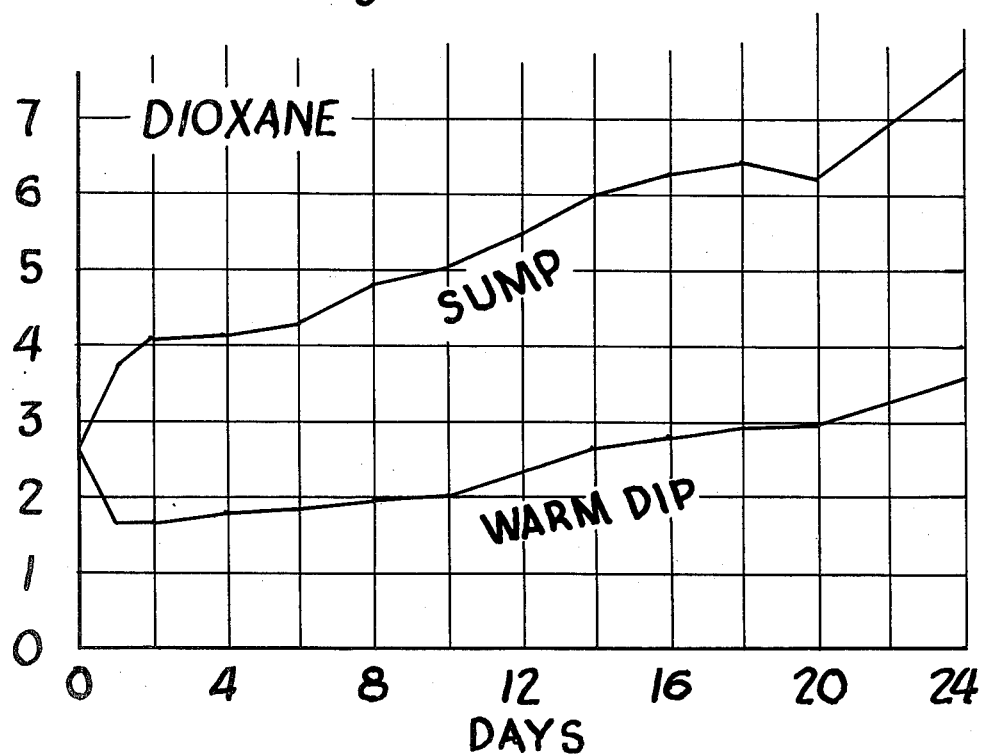
Figure 3:
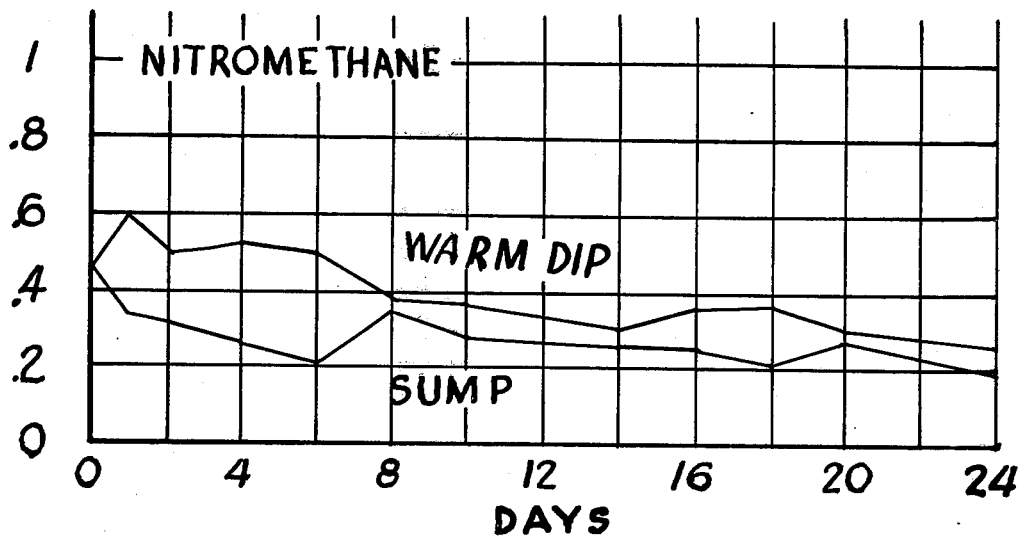
Figure 4:
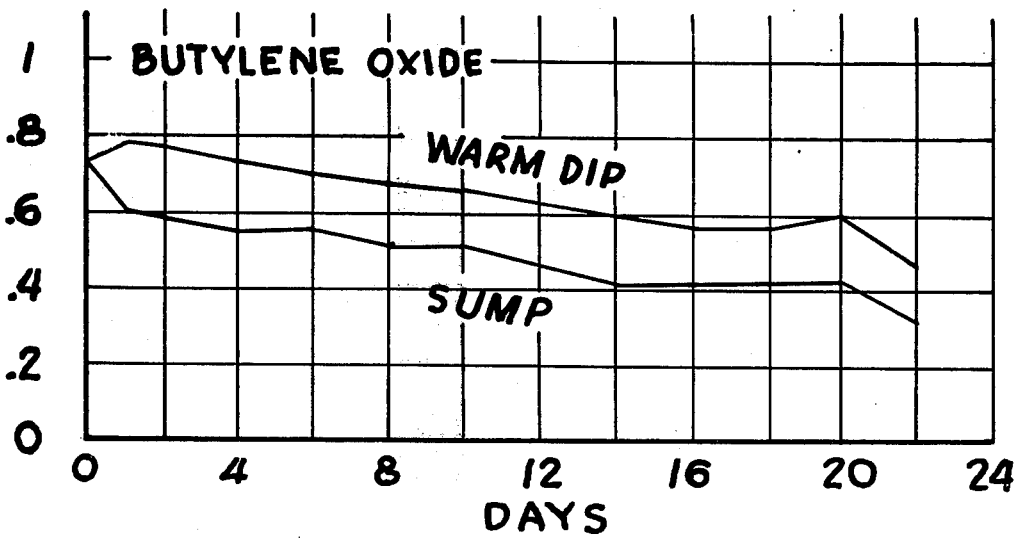

The distribution of the four inhibitors in the boiling sump and the warm dip tank is detailed in drawings FIGS. 1 through 4. The partitioning of the inhibitors followed expected patterns and there were no unusual losses during the 24 days.

Results of metal ion analysis are listed in Table III. The low levels of metal ions present in the solvent samples indicates negligible reaction between the metal chips and the solvent. Thus, the 24-day vapor degreaser test was successful and this combination of inhibitors provides excellent stability.

TABLE III

| Sample Description | Metal Analysis During Degreaser Test | | | |
|---|---|---|---|---|
| | ppm Fe | ppm Cu | ppm Al | ppm Zn |
| Virgin formulation | <1 | <0.2 | <1 | <3 |
| Warm dip tank after 18 days | <1 | <0.2 | <1 | <3 |
| Boiling sump after 18 days | <1 | <0.2 | <1 | <3 |
| Warm dip tank after 24 days | 5 | 0.2 | <1 | 5 |
| Boiling sump after 24 days | 7 | 0.4 | <1 | 5 |

DEGREASER TEST

A 2 × 5½ foot two-chamber, open-top Manpro vapor degreaser was charged with a stabilized 1,1,1-trichloroethane solvent having the following composition:
   2.5 volume percent 1,4-dioxane 1.5 volume percent t-amyl alcohol
0.15 volume percent nitromethane
0.15 volume percent nitroethane
0.75 volume percent 1,2-butylene oxide.

25 Gallons to the sump, 31 gallons to the warm dip and 29 gallons to a still associated with the degreaser. The degreaser was operated for 38 days. Solvent was pumped to and from the still although the still was not operated until the 22nd day of the test run. Solvent make-up was added on the 9, 14, 17, 24, 30 and 34 days and ½ gallon of a white cutting oil added on each of the 1, 9, 10, 13, 14, 22, 23, 24, 27, 30 and 35 days of operation. On the 16th day metals were added to the sump and the warm dip, viz;

|  | Warm Dip | Sump |
|---|---|---|
| 2024 Al | 200 gm | 200 gm |
| Steel wool | 65 gm | 65 gm |
| Mossy zinc | 500 gm | 300 gm |
| 70/30 Brass chips | 500 gm | 500 gm |

At the end of 38 days the test was stopped, the metals and solvent examined. The test was considered successful as a result of this examination.

Samples of the final composition in the warm dip and sump were taken and each sample subjected to reflux for seven days with metals as follows:

One hundred milliliters of each compartment were refluxed with either 5 grams each of 2024 Al chips, 1100 Al pellets and iron filings or 5 grams each of zinc fines and 70/30 brass. The aluminum and iron showed no evidence of attack although the zinc and brass did evidence a small amount of corrosion.

What is claimed is:

1. 1,1,1-Trichloroethane containing as the essential stabilizers from about 3.6 to about 7.6 volume percent based on the total composition volume of a mixture derived from:

1 to 3 volume percent 1,4-dioxane
1 to 3 volume percent t-amyl alcohol
0.5 to 1 volume percent 1,2-butylene oxide, and
0.2 to 0.6 volume percent of a nitroalkane selected from the group consisting of nitromethane or a mixture of nitromethane and nitroethane containing up to 75 volume percent nitroethane.

2. The composition of claim 1 wherein said dioxane is present in about 1.5 to 3.0 volume percent, said tertiary amyl alcohol is present in from 1.5 to about 3.0 volume percent, said nitroalkane is present in about 0.3 volume percent and said 1,2-butylene oxide is present in about 0.7 to 0.75 volume percent.

* * * * *